(12) United States Patent
Zhu et al.

(10) Patent No.: US 12,378,564 B2
(45) Date of Patent: Aug. 5, 2025

(54) TOMATO GLUTAREDOXIN SIGRXC9 GENE AND ITS APPLICATION

(71) Applicants: Sanya Institute of Henan University, Sanya (CN); Henan University, Kaifeng (CN)

(72) Inventors: Yingfang Zhu, Kaifeng (CN); Zhixin Jiao, Kaifeng (CN); Rui Xu, Kaifeng (CN)

(73) Assignees: Sanya Institute of Henan University, Sanya (CN); Henan University, Kaifeng (CN)

(*) Notice: Subject to any disclaimer, the term of this patent is extended or adjusted under 35 U.S.C. 154(b) by 0 days.

(21) Appl. No.: 18/081,717

(22) Filed: Dec. 15, 2022

(65) Prior Publication Data

US 2023/0340509 A1    Oct. 26, 2023

(30) Foreign Application Priority Data

Mar. 31, 2022  (CN) .................. 202210332187.X

(51) Int. Cl.
*C12N 15/82* (2006.01)
*C12N 9/22* (2006.01)
*C12N 15/11* (2006.01)

(52) U.S. Cl.
CPC ........... *C12N 15/8205* (2013.01); *C12N 9/22* (2013.01); *C12N 15/11* (2013.01); *C12N 15/8273* (2013.01); *C12N 2310/20* (2017.05)

(58) Field of Classification Search
None
See application file for complete search history.

(56) References Cited

U.S. PATENT DOCUMENTS

2015/0040272 A1* 2/2015 Park ............... C12N 15/8271
800/320.2

FOREIGN PATENT DOCUMENTS

| CN | 105861543 A | 8/2016 |
|---|---|---|
| CN | 107858371 A | 3/2018 |
| CN | 112126633 A | 12/2020 |

OTHER PUBLICATIONS

Kakeshpour, T., 2020, Tomato class II glutaredoxin mutants generated via multiplex CRISPR/Cas9 genome editing technology are susceptible to multiple abiotic stresses (Order No. 28090601). (Year: 2020).*
Solanum lycopersicum glutaredoxin-C9 (LOC101255509), mRNA, 2018, NCBI Accession No. XM_010325453. (Year: 2018).*
Xu, F., Tang, J., Gao, S., Cheng, X., Du, L., & Chu, C. (2019). Control of rice pre-harvest sprouting by glutaredoxin-mediated abscisic acid signaling. The Plant Journal, 100(5), 1036-1051 (Year: 2019).*
Li, S. (2014). Redox modulation matters: emerging functions for glutaredoxins in plant development and stress responses. Plants, 3(4), 559-582 (Year: 2014).*

* cited by examiner

*Primary Examiner* — Charles Logsdon
*Assistant Examiner* — Jessica Nicole Stockdale
(74) *Attorney, Agent, or Firm* — Nitin Kaushik

(57) ABSTRACT

The present invention discloses a tomato glutaredoxin SIGRXC9 gene and its application. The present invention first identifies the tomato glutaredoxin SIGRXC9 gene, knock out of SIGRXC9 in tomato MT (micro-Tom) by *Agrobacterium*-mediated method for function identification and obtains a result that SIGRXC9 gene deletion results in tomato hypersensitivity to chilling stress, and reduced plant height, leaf length and width, which further demonstrates that SIGRXC9 plays an important role in controlling development and response to low-temperature stress.

7 Claims, 3 Drawing Sheets
Specification includes a Sequence Listing.

SEQUENCE LISTING

```
Sequence total quantity: 9
SEQ ID NO: 1            moltype = DNA  length = 444
FEATURE                 Location/Qualifiers
source                  1..444
                        mol_type = genomic DNA
                        organism = Solanum lycopersicum
SEQUENCE: 1
atgcaacaag cacttcctta caagtcatca tgtatatctc taacaccaag agttgatcga   60
catcatcgtg taagtaatat caattcatta ttatacgtta aaggttcaaa agaagaattg  120
aataacgttg ttaaggataa cgcggttatc gttgtgggaa gacgaggttg ttgtatgagc  180
catgttgtga aacgtttact tcattgtctc ggagcaaatc ctgccattta tgaaatcgag  240
gaagacgatg aaaacgaagt ggttgatgag ttggagaata ttatcgtcgc cggaggtagt  300
gatcggaaag acaccggacg gttgcaattt ccggcggtgt tcgtcggagg ggagctgttt  360
ggtggattgg atcggattat ggcggctcat attaccggcg agttgactcc tgtgttgaaa  420
aaggctggag ccttatggct ttga                                         444

SEQ ID NO: 2            moltype = AA  length = 147
FEATURE                 Location/Qualifiers
source                  1..147
                        mol_type = protein
                        organism = Solanum lycopersicum
SEQUENCE: 2
QQALPYKSSC ISLTPRVDRH HRVSNINSLL YVKGSKEELN NVVKDNAVIV VGRRGCCMSH   60
VVKRLLHCLG ANPAIYEIEE DDENEVVDEL ENIIVAGGSD RKDTGRLQFP AVFVGGELFG  120
GLDRIMAAHI TGELTPVLKK KAGALWL                                      147

SEQ ID NO: 3            moltype = DNA  length = 21
FEATURE                 Location/Qualifiers
source                  1..21
                        mol_type = other DNA
                        note = FWD_primer_SlGRXC9
                        organism = synthetic construct
SEQUENCE: 3
atgcaacaag cacttcctta c                                             21

SEQ ID NO: 4            moltype = DNA  length = 21
FEATURE                 Location/Qualifiers
source                  1..21
                        mol_type = other DNA
                        note = REV_primer_SlGRXC9
```

```
                        organism = synthetic construct
SEQUENCE: 4
tcaaagccat aaggctccag c                                              21

SEQ ID NO: 5            moltype = DNA  length = 23
FEATURE                 Location/Qualifiers
source                  1..23
                        mol_type = other DNA
                        organism = synthetic construct
SEQUENCE: 5
taacgttgtt aaggataacg cgg                                            23

SEQ ID NO: 6            moltype = DNA  length = 445
FEATURE                 Location/Qualifiers
source                  1..445
                        mol_type = other DNA
                        organism = Solanum lycopersicum
SEQUENCE: 6
atgcaacaag cacttcctta caagtcatca tgtatatctc taacaccaag agttgatcga    60
catcatcgtg taagtaatat caattcatta ttatacgtta aaggttcaaa agaagaattg    120
aataacgttg ttaaggataa acgcggttat cgttgtggga agacgaggtt gttgtatgag    180
ccatgtgtg aaacgtttac ttcattgtct cggagcaaat cctgccattt atgaaatcga    240
ggaagacgat gaaaacgaag tggttgatga gttggagaat attatcgtcg ccggaggtag    300
tgatcggaaa gacaccggac ggttgcaatt tccggcggtg ttcgtcggag gggagctgtt    360
tggtggattg gatcggatta tggcggctca tattaccggc gagttgactc ctgtgttgaa    420
aaaggctgga gccttatggc tttga                                          445

SEQ ID NO: 7            moltype = DNA  length = 439
FEATURE                 Location/Qualifiers
source                  1..439
                        mol_type = other DNA
                        organism = Solanum lycopersicum
SEQUENCE: 7
atgcaacaag cacttcctta caagtcatca tgtatatctc taacaccaag agttgatcga    60
catcatcgtg taagtaatat caattcatta ttatacgtta aaggttcaaa agaagaattg    120
aataacgttg ttaaacgcgg ttatcgttgt gggaagacga ggttgttgta tgagccatgt    180
tgtgaaacgt ttacttcatt gtctcggagc aaatcctgcc atttatgaaa tcgaggaaga    240
cgatgaaaac gaagtggttg atgagttgga gaatattatc gtcgccgag gtagtgatcg    300
gaaagacacc ggacggttgc aatttccggc ggtgttcgtc ggaggggagc tgtttggtgg    360
attggatcgg attatggcgg ctcatattac cggcgagttg actcctgtgt tgaaaaaggc    420
tggagcctta tggctttga                                                 439

SEQ ID NO: 8            moltype = DNA  length = 21
FEATURE                 Location/Qualifiers
source                  1..21
                        mol_type = other DNA
                        note = FWD_primer_SlGRXC9-g1
                        organism = synthetic construct
SEQUENCE: 8
gttgatcgac atcatcgtgt a                                              21

SEQ ID NO: 9            moltype = DNA  length = 21
FEATURE                 Location/Qualifiers
source                  1..21
                        mol_type = other DNA
                        note = REV_primer_SlGRXC9-g1
                        organism = synthetic construct
SEQUENCE: 9
cgatttcata aatggcagga t                                              21
```

TOMATO GLUTAREDOXIN SIGRXC9 GENE AND ITS APPLICATION

CROSS-REFERENCE TO RELATED APPLICATIONS

The application claims priority to Chinese patent application No. 202210332187.X, filed on Mar. 31, 2022, the entire contents of which are incorporated herein by reference.

SEQUENCE LISTING

The sequence listing xml file submitted herewith, named "Sequence_Listing_WI-US22-4255-P.xml", created on Apr. 9, 2024, and having a file size of 11,199 bytes, is incorporated by reference herein.

TECHNICAL FIELD

The present invention belongs to the field of biotechnology, and particularly relates to a tomato glutaredoxin SIGRXC9 gene and an application.

BACKGROUND

Low-temperature stress severely affects the quality and the yield of tomato and other horticultural crops, which has become one of bottleneck problems limiting development of facility agriculture. CRISPR-Cas9 has become a powerful genome editing technology to accurately modify genes in plants including tomato. If the gene edited plant is sensitive to low-temperature treatment, the gene is overexpressed in the plant; and if the tolerance of the gene edited plant to low-temperature treatment is strengthened, the gene edited plant is directly applied to production. The present invention is intended to improve the resistance of vegetable crops under the adverse environmental conditions by means of genetic engineering, which will be of great scientific and practical significance in increasing the yield, the quality and the economic benefit of vegetables and guaranteeing balanced supply of the vegetables in China.

The tomato is one of most important fruit crops and model crops in the world, and their growth and development are prone to being affected by the adverse environmental conditions. With the tomato genomic sequencing was conducted in 2012, scientists employed research means of reverse genetics, and many tomato genes responding to adversity stress were reported. Reactive oxygen species (ROS) is a kind of small signal molecules normally metabolized in plant bodies and plays an important role in signal transduction of growth, development and stress resistance response of plants. However, accumulation of too much ROS can severely affect growth and development of the plants and results in oxidative stress. Glutaredoxins (GRXs) are redox proteins for a class of small molecules, can regulate a redox state of proteins to maintain the activity of the proteins and play an important role in resistance to oxidative stress and growth and development response of the plants. The GRX is also referred to as thioltransferase previously, is first discovered in mammals and generally comprises about 100 amino acid residues. A protein with similar structure and functions is discovered in *Escherichia coli* and is named as GRX due to dependency on reduction activity of GSH. GRXs are of a multigene family and may be classified into CPYC type, CGFS type and CC type according to their sequences of active sites. Tomato glutaredoxin SIGRXC9 in the present invention belongs to the CC type. At present, a research on *Arabidopsis* as a model plant shows that GRXC9 plays an important role in controlling development of petioles, fungus resistance and defense response. There is still no report for whether GRXC9 in the plants has other applications at present, particularly there is rarely report for a deep research on a related mechanism of the tomatoes responding to chilling stress. Therefore, it is of great significance in researching effects of the redox state of the proteins on growth, development and stress resistance of the tomatoes on the gene level.

SUMMARY

One of the objectives of the present invention is to provide a tomato glutaredoxin SIGRXC9 gene.

A second objective of the present invention is to provide an application of the tomato glutaredoxin SIGRXC9 gene.

In order to achieve the above objectives, the present invention employs the following technical solution:

A tomato glutaredoxin SIGRXC9 gene comprises a nucleotide sequence shown as SEQ ID NO.1; and the nucleotide sequence is composed of 444 bases and encodes totally 147 amino acids with a sequence shown as SEQ ID NO.2.

Proteins encoded by the above glutaredoxin SIGRXC9 gene is selected from a group consisting of:
(1) a protein having an amino acid sequence shown as SEQ ID NO. 2;
(2) a protein having an amino acid sequence subjected to substitution, deletion and/or addition of one or more (for example, 1-30; preferably, 1-20; and more preferably, 1-10, such as 5 and 3) amino acid residues in the amino acid sequence shown as SEQ ID NO. 2, having a function of the protein (1) and derived from the protein (1); and
(3) a protein comprising an amino acid sequence having a homology of 80% (preferably, 90% or higher, such as 95%, 98%, 99% or higher) or higher with the sequence of the protein defined in (1), having a function of the protein (1) and derived from the protein (1).

That is to say, functions of the gene claimed by the present invention comprise the above tomato glutaredoxin SIGRXC9 gene and further comprise homologous genes comprising amino acid sequences having a high homology (such as a homology of 40% or higher; preferably, 50% or higher; preferably, 60% or higher; more preferably, 70% or higher; more preferably, 80% or higher; more preferably, 90% or higher; more preferably, 95% or higher; and more preferably, 98% or higher) with SEQ ID NO. 1.

The primary objective of the present invention is to clone and identify the tomato glutaredoxin SIGRXC9 on the molecular level, so as to provide a fundamental basis for research on parsing a related mechanism of controlling chilling stress response, growth and development of the tomatoes. The present invention further discloses applications of the above tomato glutaredoxin SIGRXC9 gene in expressing following aspects of:
(1) dwarfed plants; and
(2) a phenotype sensitive to chilling stress treatment.

In the above applications, dwarfed plants and plants with symptoms of being sensitive to chilling stress are obtained by knocking out the above gene,
wherein a dwarfed phenotype comprises reduction in average plant height; a small leaf phenotype comprises reduction in both length and width of a leaf, and a chilling stress phenotype comprises a 4° C. treatment sensitive phenotype.

As an implementation, polynucleotides are cloned into a CRISRP vector by a conventional method, and a recombinant vector with a foreign gene is introduced into a plant cell capable of expressing the SIGRXC9 protein, to result in deletion of the SIGRXC9 protein in the plant cell. An SIGRXC9 gene deleted mutant plant may be obtained by enabling the plant cell to be regenerated into a plant; and a recombinant plasmid is transferred into the plant with *Agrobacterium* transformation.

As an experiment proves that after expression of the SIGRXC9 gene is inhibited by a gene editing technology, the plant is expressed as being sensitive to low-temperature treatment, that is to say, the cold tolerance of the plant is weakened. From the above, the SIGRXC9 gene has the effect of strengthening the cold tolerance of the plant.

According to this characteristic, the cold-tolerant plant may be obtained with a transgenosis mode; and specifically, a transgenic plant may be obtained by introducing the SIGRXC9 gene into a target plant, and the cold tolerance of the plant is stronger than that of the target plant.

Specifically, the SIGRXC9 gene may be introduced into the target plant by virtue of a recombinant expression vector. In this method, the plant cell or tissue is transformed with the recombinant expression vector by using conventional biological methods such as a Ti plasmid, an Ri plasmid, a plant virus vector, direction DNA transformation, microinjection, electric conductance and *Agrobacterium* mediation, and the transformed plant tissue is cultured into a plant.

Specifically, in order to improve the good traits of the plant, the present invention further claims a new plant breeding method, comprising the following step (1), (2) or (3):
  (1) obtaining a plant with the cold tolerance stronger than that of the target plant by improving the activity of the SIGRXC9 protein in the target plant;
  (2) obtaining a plant with the cold tolerance stronger than that of the target plant by promoting expression of the SIGRXC9 gene in the target plant; and
  (3) obtaining a dwarfed plant and/or a plant with a symptom of being sensitive to low-temperature treatment by inhibiting the expression of the SIGRXC9 gene in the target plant.

An implementation mode of "promoting the expression of the SIGRXC9 gene in the target plant" may be as following (1) or (2) or (3):
  (1) introducing a GmPCBER4 gene into the target plant;
  (2) introducing a strong promoter and/or an enhancer; and
  (3) other common methods in the art.

Inhibiting the expression of the SIGRXC9 gene in the target plant may employ a mode of knocking out the SIGRXC9 gene; and the mode of knocking out the SIGRXC9 gene may employ the gene editing technology, wherein the target plant in the present invention is the tomato.

The target gene is used for genetic recombination, a change on traits of a recipient cell and obtaining of a gene of an expected expression product in design and operation of gene engineering. The target gene may be from an organism self or different organisms.

In the present invention, there is no particular limitation to plant suitable for the present invention, as long as the plant adapts to transformation operation of genes, such as various crops, flower plants or forestry plants. The plant, for example, may be (not limited to): a dicotyledon, a monocotyledon or a gymnosperm.

Preferably, the "plant" comprises, but is not limited to, the tomato belonging to the family Solanaceae, and all the plants having this gene or a gene homologous with this gene are applicable. The target gene is particularly suitable for a plant required to be dwarfed, such as an apple tree and a cherry tree of Rosaceae, and the dwarfed plant may be obtained by knocking out the SIGRXC9 gene.

The "plant" in the present invention comprises a whole plant and a parent and different portions (including a seed, a fruit, a bud, a stem, a leaf, a root (including a tuber), a flower, a tissue and an organ) of the plant thereof; and these different portions all have our target gene or nucleic acid. The "plant" mentioned herein further comprises a plant cell, a suspension culture, a callus, an embryo, a meristem zone, a gametophyte, a sporophore, pollens and a microspore; and similarly, each of foregoing objects contains the target gene/nucleic acid.

The present invention comprises any plant cell, or any plant obtained or obtainable by the methods therein, all plant portions and a propagule thereof. This patent also contains a transfection cell, a tissue, an organ or an intact plant obtained by any foregoing method. The only requirement is that an offspring shows same genotypic or phenotypic features; and offsprings obtained by using the methods in this patent have the same characteristics.

The present invention also extends to the portions, which may be harvested, of the above plants, but not limited to, the seed, the leaf, the fruit, the flower, the stem, the root, a rhizome, the tuber and a corm. Meanwhile, the present invention further relates to other derivatives of the plant after being harvested, such as dry granules or powder, oil, fat and fatty acid, starch or a protein. The present invention further relates to foods or a food additive obtained from a related plant.

The present invention has advantages that:
  (1) The inventor uses the *Agrobacterium*-mediated method to knock out SIGRXC9 from the tomato MT for function identification, which facilitates illustration of the effect of SIGRXC9 in controlling a plant type and chilling stress response from a molecular mechanism and plays an active guidance role in further illustrating a tomato plant type control mechanism and cultivating a new variety of low-temperature tolerance tomatoes.
  (2) Deletion of the SIGRXC9 gene may severely affect growth and development of various organs of a whole tomato plant, showing symptoms of reduction in plant height, the small leaf phenotype and the like and the symptom of being sensitive to low-temperature treatment, which also embodies that SIGRXC9 plays a key role in the development progress of the plant.
  (3) For some plants required to be dwarfed, such as fruit trees and ornamental plants (unnecessary nutrition assimilation is reduced, so that light energy and soil fertility are fully used, fruiting is conducted in advance, the yield is increased or the ornamental effect is improved), a new way may be provided for breeding for dwarfed plants by knocking out the SIGRXC9 gene.
  (4) The cold-tolerant plant may be obtained with the transgenosis mode; and specifically, the transgenic plant may be obtained by introducing the SIGRXC9 gene into the target plant, and the cold tolerance of the

DETAILED DESCRIPTION OF THE EMBODIMENTS

Figure 1:
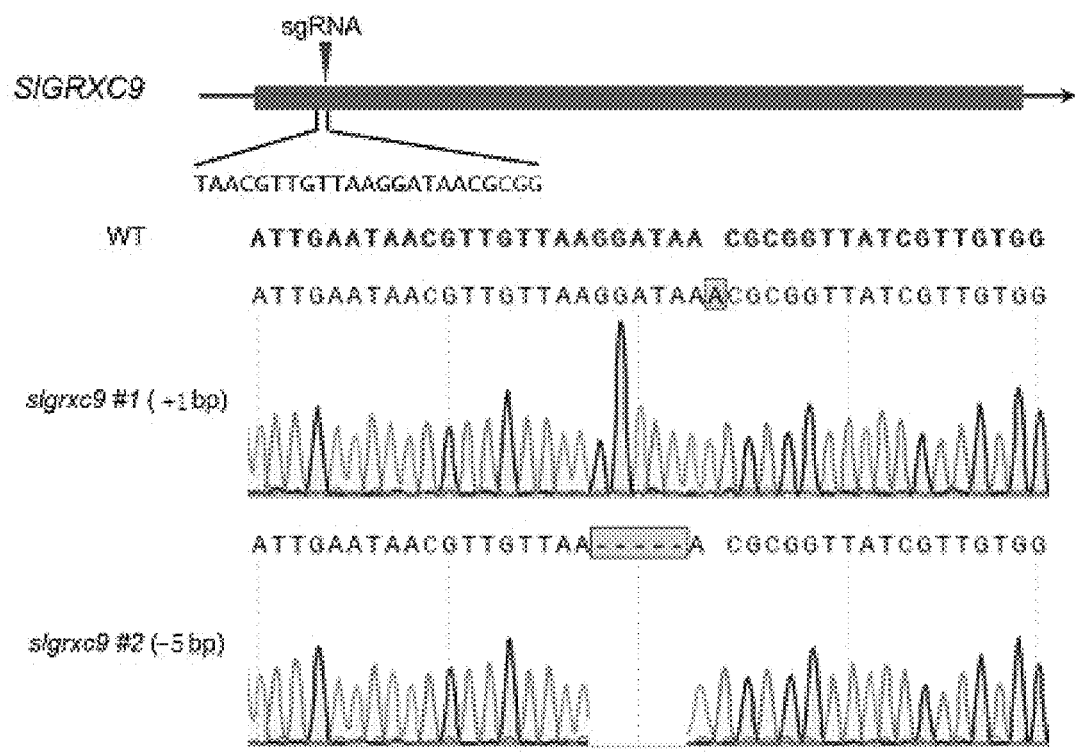
FIG. 1 is a diagram showing two different edited types of SlGRXC9 knockout lines comprising nucleotide sequences of SEQ ID No. 6 and SEQ ID No. 7.

The present invention will be described in detail below through specific embodiments. The embodiments are provided here for making the present invention more thorough and conveying the scope of the present invention to those skilled in the art.

If not otherwise specified, the technical means used in the embodiments are conventional means well known by those skilled in the art. If not otherwise specified, the test methods in the following embodiments are all conventional methods. If not otherwise specified, the used agents and materials may all commercially available.

Unless defined otherwise, all unprofessional and scientific terms used herein have the same meaning familiar to those skilled in the art. In addition, any method and material similar or equal to recorded contents may all be applied to the present invention. The preferred implementation methods and materials herein are exemplary only.

Unless otherwise stated, implementation of the present invention will use a conventional botanical technology, microorganisms, tissue culture, molecular biology, chemistry, biochemistry, DNA recombination and a bioinformatics technology apparent to those skilled in the art. These technologies are fully explained in disclosed literatures. In addition, the methods, such as DNA extraction, construction of a phylogenetic tree, a gene editing method, construction of a gene editing vector and obtaining of a gene edited plant, employed in the present invention can be realized by using the disclosed method in existing literatures, in addition to the methods employed in the following embodiments.

Terms "nucleic acid", "nucleotide sequence", "nucleotide", "nucleic acid molecule" or "polynucleotide" used herein refer to isolated DNA molecules (for example, cDNA or genomic DNA), RNA molecules (for example, messenger RNA), a natural type, a mutation type, synthetic DNA or RNA molecules, DNA or RNA molecules formed by nucleotide analogues, and a single or double stranded structure. These nucleic acids or polynucleotides comprise gene coding sequences, anti-sense sequences and regulatory sequences of noncoding regions, but are not limited thereto. These terms comprise one gene. "Gene" or "gene sequence" refers broadly to a functional DNA nucleotide sequence. Therefore, the gene may comprise an intron and an exon in a genomic sequence, and/or comprise an encoding sequence in cDNA, and/or comprise cDNA and a regulatory sequence thereof. In a particular embodiment, for example, related to an isolated nucleotide sequence, it is preferentially defaulted as cDNA.

In addition, for more intuitively understanding the technical solution of the present invention, the technical terms of the present invention are explained as follows:

"Gene editing" is an emerging gene function technology of accurately modifying a specific target sequence of a genome of an organism.

"Gene knockout" is a technology of targeted integration of a foreign gene into a certain determined site on a target cell genome through homologous recombination to achieve the objective of targeted modification on a certain gene on a chromosome.

A "mutant" refers to a mutating individual, having different characteristics of a phenotype from a wild type.

An "expression vector" refers to a vector which adds an expression element (such as a promoter, RBS and a terminator) on the basis of a basic skeleton of a cloning vector to enable the target gene to make expression.

The inventor obtains a sequence of the tomato glutaredoxin SlGRXC9 gene through the bioinformatics technology on the basis of a tomato genome. The present invention introduces the sequence into a wild type tomato after ligating the sequence to a plant editing vector for phenotype identification.

Compared with the traditional transgenic technology, a CRISPR/Cas9 gene editing technology has many advantages. The traditional transgenic technology is that a foreign target gene is introduced into an organism to change traits of a plant, and an insertion site of a target gene into a receptor genome is random; whereas, for the CRISPR/Cas9 gene editing technology, there is no introduction of the foreign gene, only an endogenous gene is modified, and this technology is safer and more efficient. Next, the CRISPR/Cas9 gene editing technology may edit multiple sites at the same time and can precisely control a mutation or insertion site, which cannot be completed by the traditional transgenic technology. In addition, the traditional transgenic technology can only down-regulate an expression level of the gene on the RNA level, cannot completely inhibit transcription of the gene and shows genetic instability in the gene; whereas the CRISPR/Cas9 gene editing technology can achieve a mutation in the target gene and is more stable and reliable.

1. Isolation of SlGRXC9 gene

Extraction of total RNA from a MT tomato seedling: extraction follows instructions of a Trizol extracting reagent (TaKaRa), a first strand cDNA synthesis follows instructions of PrimerScript™ II 1st Strand cDNA Synthesis Kit (TaKaRa) as a reverse transcription kit. With cDNA of a tomato as a template, Primer STAR Max high-fidelity DNA polymerase amplification (TaKaRa) is used with an annealing temperature of 58° C.

With following sequences as primers, a full-length sequence of the SlGRXC9 gene is obtained with PCR amplification. The full-length sequence of the SlGRXC9 gene is shown as SEQID NO. 1 in a sequence table, is 444 bp in total and encodes an amino acid sequence (shown as SEQ ID NO. 2 in a sequence table and having 147 amino acids in total) of the protein.

Primer sequences are as follows:
SlGRXC9-F: 5'-ATGCAACAAGCACTTCCTTAC-3' (SEQ ID No. 3); and
SlGRXC9-R: 5'-TCAAAGCCATAAGGCTCCAGC-3' (SEQ ID No. 4).

2. Test on Function Identification on SlGRXC9 Gene

To study if SlGRXC9 gene controls the tolerance of the tomato to low temperature, a function of the SlGRXC9 gene is identified through a tomato in a gene knockout line. 2.1 Construction of recombinant vector A target site is selected from a CDS region of the SlGRXC9 gene, i.e. TAACGTTGTTAAGGATAACGCGG (SEQ ID No. 5). A purified sgRNA-SlGRXC9 fragment is recovered and is ligated to a vector subjected to digestion, so as to obtain an SlGRXC9-CRISPR recombinant plasmid. Genetic transformation is conducted on the tomato with *Agrobacterium* mediation to obtain a tomato SlGRXC9-CRISPR transformed seedling.

2.2 Screening and phenotype analysis of transgenic positive plant 100 mg of leaves of a resistant plant is taken, and genomic total DNA is extracted with a CTAB method. Specific primers are designed according to a sequence of the target gene, subjected to PCR amplification and sent for sequencing.

Primer sequences are as follows:

SlGRXC9-g1-F: 5'-GTTGATCGACATCATCGTGTA-3' (SEQ ID No. 8); and

SlGRXC9-g1-R: 5'-CGATTTCATAAATGGCAGGAT-3' (SEQ ID No. 9).

Through identification with sequencing, two different edited types of SlGRXC9 knockout lines are obtain in total, such as slgrxc9 #1 (+1 bp) having a nucleotide sequence of SEQ ID No. 6_and slgrxc9 #2 (−5 bp) having a nucleotide sequence of SEQ ID No. 7 (FIG. 1).

Figure 2:
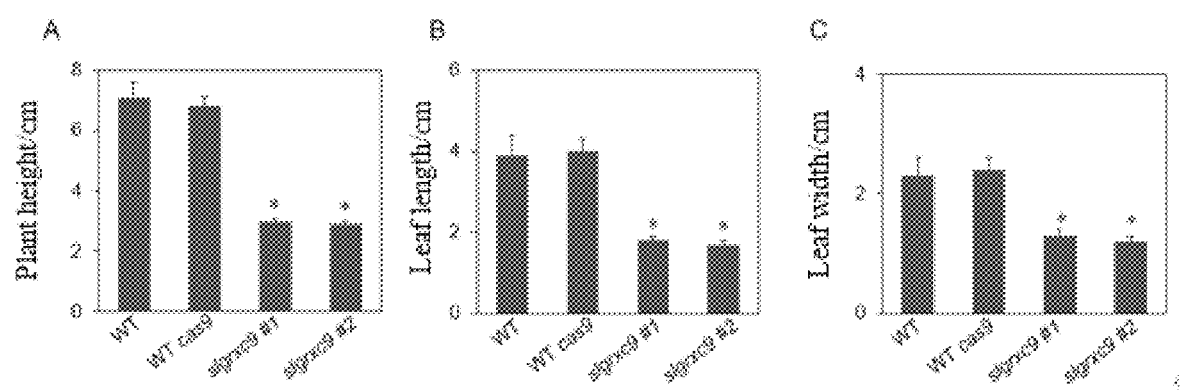
FIG. 2 is a diagram showing development phenotypes of a wild type tomato WT, WT cas9, slgrxc9 #1 and slgrxc9 #2.

FIG. 2 is an observation diagram of phenotypes of tomato WT (wild type), WT cas9 (empty vector control), slgrxc9 #1 (+1 bp) and slgrxc9 #2 (−5 bp). From FIG. 2, an average plant height of the SlGRXC9 knockout line is significantly smaller than wild type and the empty vector control, and a dwarfed phenotype is formed; and for the SlGRXC9 gene knockout line, growth of a leaf is significantly inhibited, and compared with the wild type and the empty vector control, a length and a width of the leaf are significantly lowered.

Figure 3:
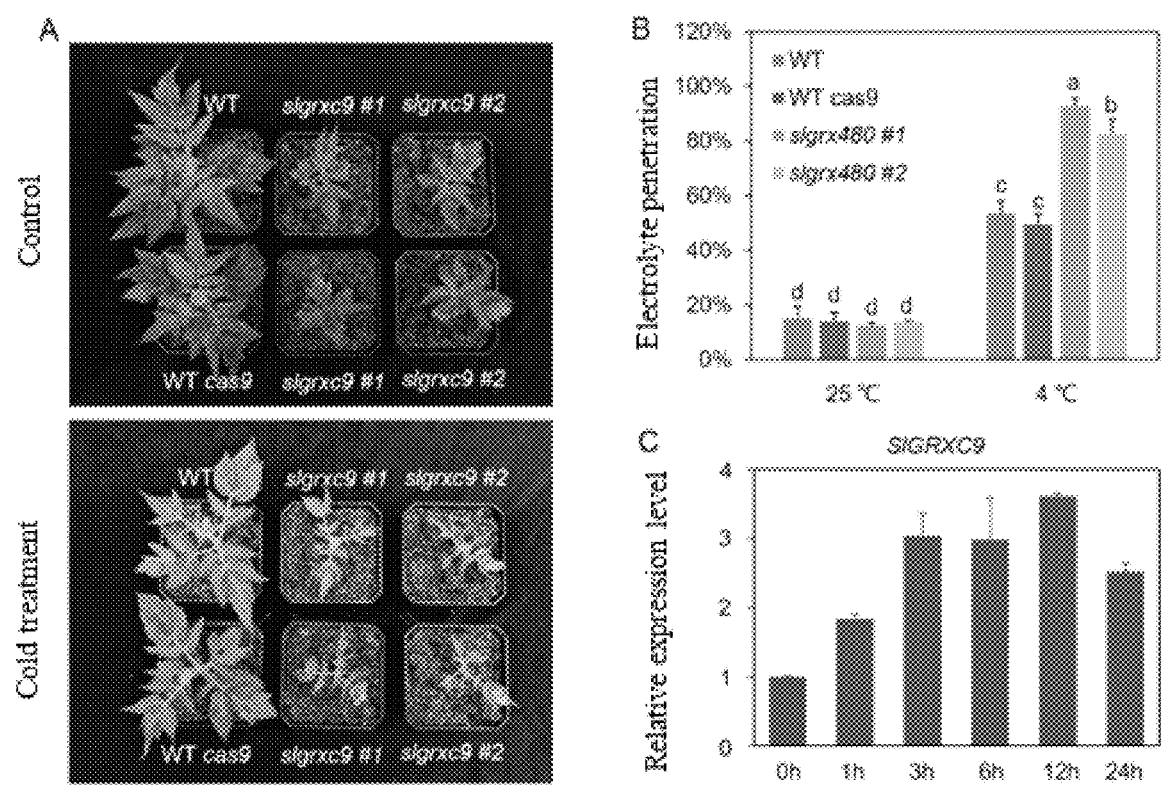
FIG. 3 is a diagram showing chilling stress treatment phenotypes of a wild type tomato WT, WT cas9, slgrxc9 #1 and slgrxc9 #2, wherein in the drawings, WT: wild type, WT cas9: empty vector control, and slgrxc9 #1 and slgrxc9 #2: mutant plants.

FIG. 3A is diagram, in which wild type tomato WT (wild type), WT cas9 (empty vector control), slgrxc9 #1 (+1 bp) and slgrxc9 #2 (−5 bp) are treated in a cold room at a low temperature of 4° C. From FIG. 3A, compared with the wild type and the empty vector control, the SlGRXC9 gene knockout line is more sensitive to low-temperature treatment. Therefore, a numerical value of electrolyte penetration of a physiological phenotype is larger (FIG. 3B). In addition, FIG. 3C shows that an expression level of the SlGRXC9 gene is significantly induced by low-temperature treatment (Actin7 serves as an internal reference).

In general, compared with the wild type, a plant in the gene knockout line shows reduced plant height, leaf length and leaf width, and dwarfed phenotype. In addition, the SlGRXC9 gene has obvious effects on the low-temperature tolerance of the tomato.

The above-mentioned embodiments are only preferred embodiments of the present invention, and are only used to explain the present invention rather than limiting the scope of the present invention. To those skilled in the art, other implementations may be easily made through substitutions or variations according to the technical contents disclosed in this specification certainly. Therefore, all changes, improvements and the like made in the principle of the present invention should be encompassed by the protection scope of the present invention.

What is claimed is:

1. A method for improving cold tolerance of plants, wherein a transgenic plant is obtained by introducing a tomato glutaredoxin SlGRXC9 gene into a target plant using a recombinant expression vector; the cold tolerance of the transgenic plant is improved; and a nucleotide sequence of the SlGRXC9 gene is shown as SEQ ID NO. 1.

2. The method according to claim 1, wherein the plant comprises tomato, an apple tree, or a cherry tree.

3. A method for obtaining a dwarfed tomato plant and/or a tomato plant with a symptom of being sensitive to low-temperature treatment, wherein the method inhibits the functional expression of the tomato glutaredoxin SlGRXC9 gene, and the nucleotide sequence of the SlGRXC9 gene is shown as SEQ ID NO.1.

4. The method according to claim 3, wherein a dwarfed phenotype comprises reduction in average plant height, and reduction in length and width of a leaf.

5. The method according to claim 3, wherein the functional expression of the tomato glutaredoxin SlGRXC9 gene is inhibited by knocking out the SlGRXC9 gene.

6. The method according to claim 5, wherein the SlGRXC9 gene is knocked out by a gene editing technology.

7. The method according to claim 6, wherein a SlGRXC9-CRISPR recombinant plasmid is obtained by the gene editing technology.

* * * * *